US012648675B2

(12) United States Patent
Sandler

(10) Patent No.: US 12,648,675 B2
(45) Date of Patent: Jun. 9, 2026

(54) TECHNOLOGY CONFIGURED TO MONITOR CORRECT UTILIZATION OF A DISPENSED SUBSTANCE, INCLUDING DISPENSING UNITS HAVING ENVIRONMENTAL SENSORS

(71) Applicant: Hygiene Habits Pty Ltd, Queenscliff (AU)

(72) Inventor: Isaac Sandler, Queenscliff (AU)

(73) Assignee: Hygiene Habits Pty Ltd, Queenscliff (AU)

( * ) Notice: Subject to any disclaimer, the term of this patent is extended or adjusted under 35 U.S.C. 154(b) by 142 days.

(21) Appl. No.: 18/002,324

(22) PCT Filed: May 10, 2021

(86) PCT No.: PCT/AU2021/050428
§ 371 (c)(1),
(2) Date: Dec. 19, 2022

(87) PCT Pub. No.: WO2021/226658
PCT Pub. Date: Nov. 18, 2021

(65) Prior Publication Data
US 2023/0346172 A1     Nov. 2, 2023

(30) Foreign Application Priority Data

May 9, 2020     (AU) ................................ 2020901495
May 27, 2020    (AU) ................................ 2020901712
(Continued)

(51) Int. Cl.
A47K 5/12     (2006.01)
A47K 5/18     (2006.01)
G16H 40/20    (2018.01)

(52) U.S. Cl.
CPC .......... *A47K 5/1217* (2013.01); *A47K 5/1202* (2013.01); *A47K 5/18* (2013.01); *G16H 40/20* (2018.01)

(58) Field of Classification Search
CPC ...... A47K 5/12; A47K 5/1217; A47K 5/1205; A47K 5/1207; A47K 5/1211;
(Continued)

(56) References Cited

U.S. PATENT DOCUMENTS 6,417,773 B1     7/2002   Vlahos et al.
6,426,701 B1     7/2002   Levy et al.
(Continued)

FOREIGN PATENT DOCUMENTS

WO     2019/106078 A1     6/2019
WO     2020/044351 A1     3/2020

OTHER PUBLICATIONS

International Search Report for International Application No. PCT. AU2021/050428 dated Jun. 21, 2021, 7 pages.
(Continued)

*Primary Examiner* — Charles P. Cheyney
(74) *Attorney, Agent, or Firm* — TraskBritt

(57)     ABSTRACT

Technology is configured to monitor correct utilization of a dispensed substance, including dispensing units having environmental sensors. For example, this may include soap dispensers configured to monitor handwashing activity, and toothpaste dispensers configured to monitor brushing activity. Embodiments include both base units that are configured to operate with separate dispensing containers, and containers having electronic components built in.

14 Claims, 5 Drawing Sheets

(30)            Foreign Application Priority Data

Dec. 7, 2020    (AU) ............................... 2020904527
Feb. 14, 2021    (AU) ............................... 2021900361

(58) Field of Classification Search
CPC .... A47K 5/1218; A47K 5/1202; G01G 21/22;
G08B 5/38; A61M 15/009; A61M 15/008
USPC ...................................... 222/23, 25, 39, 113
See application file for complete search history.

(56)              References Cited

U.S. PATENT DOCUMENTS

| | | | | |
|---|---|---|---|---|
| 7,315,245 | B2 * | 1/2008 | Lynn | .................. G09B 19/0076 |
| | | | | 340/573.1 |
| 7,782,214 | B1 * | 8/2010 | Lynn | .................... A47K 5/1217 |
| | | | | 340/572.1 |
| 8,816,860 | B2 * | 8/2014 | Ophardt | ................. G16H 40/20 |
| | | | | 340/286.07 |
| 9,117,361 | B1 * | 8/2015 | Hennigan | ............. G08B 21/245 |
| 9,218,734 | B2 | 12/2015 | Wallace et al. | |
| 9,536,415 | B2 | 1/2017 | De Luca et al. | |
| 10,025,908 | B1 | 7/2018 | Orellano et al. | |
| 10,039,423 | B2 * | 8/2018 | Schultz | ................ A47K 5/1211 |
| 10,235,865 | B2 | 3/2019 | Thyroff | |
| 10,332,382 | B2 | 6/2019 | Thyroff | |
| 11,961,385 | B2 | 4/2024 | Paliath-Pathiyal et al. | |
| 12,171,382 | B2 | 12/2024 | Mahaffey et al. | |
| 2006/0249530 | A1 | 11/2006 | Ho | |

| | | | | |
|---|---|---|---|---|
| 2007/0182571 | A1 | 8/2007 | Kennish et al. | |
| 2007/0289993 | A1 | 12/2007 | Nanda | |
| 2009/0166378 | A1 * | 7/2009 | Stilley | ................. B05B 11/0005 |
| | | | | 222/113 |
| 2011/0180564 | A1 * | 7/2011 | Jones | ........................ A47K 5/12 |
| | | | | 222/113 |
| 2013/0098941 | A1 * | 4/2013 | Wegelin | ............... A47K 5/1205 |
| | | | | 222/23 |
| 2013/0099900 | A1 * | 4/2013 | Pulvermacher | ....... B05B 11/108 |
| | | | | 340/10.42 |
| 2014/0158714 | A1 * | 6/2014 | Snodgrass | ............ A47K 5/1217 |
| | | | | 222/183 |
| 2014/0197194 | A1 * | 7/2014 | Wegelin | ............... A47K 5/1201 |
| | | | | 222/38 |
| 2014/0311239 | A1 * | 10/2014 | Marjanovic | ............ G01G 21/28 |
| | | | | 73/296 |
| 2016/0068315 | A1 * | 3/2016 | Hintz | ..................... B65D 51/24 |
| | | | | 340/687 |
| 2018/0184857 | A1 | 7/2018 | Pai | |
| 2019/0043337 | A1 | 2/2019 | Liu et al. | |
| 2019/0069730 | A1 | 3/2019 | Ophardt et al. | |
| 2019/0231993 | A1 | 8/2019 | Van Sickle et al. | |
| 2019/0378395 | A1 | 12/2019 | Pi | |
| 2020/0074836 | A1 | 3/2020 | Kolavennu et al. | |

OTHER PUBLICATIONS

International Written Opinion for International Application No. PCT.AU2021/050428 dated Jun. 21, 2021, 6 pages.

* cited by examiner

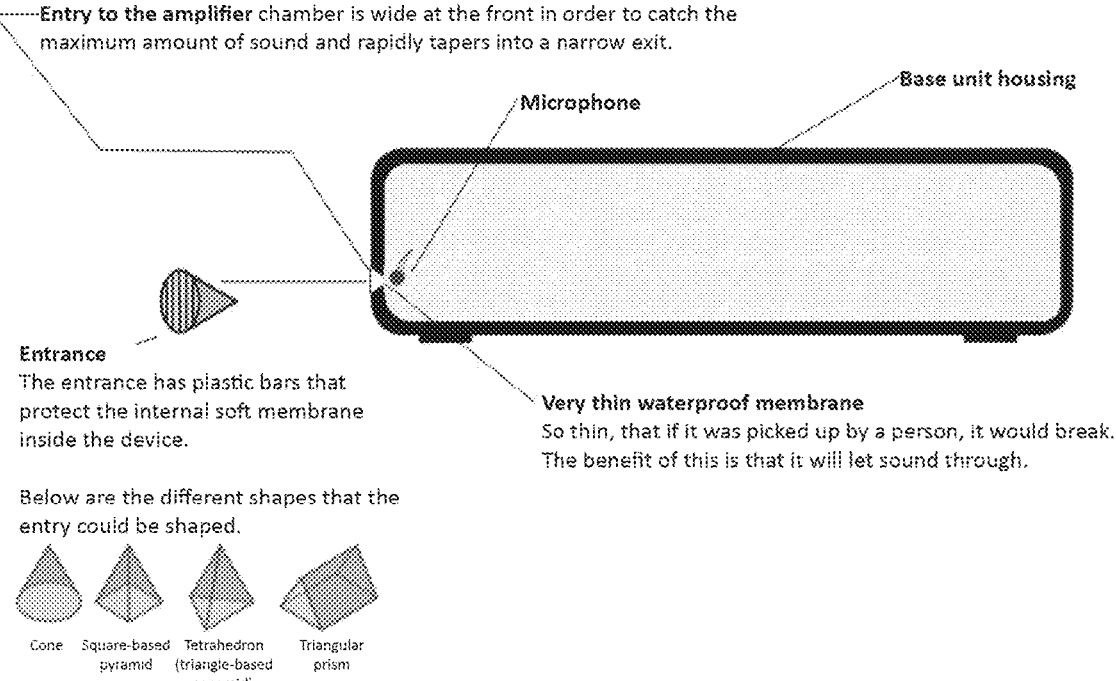

Entry to the amplifier chamber is wide at the front in order to catch the maximum amount of sound and rapidly tapers into a narrow exit.

Microphone

Base unit housing

Entrance
The entrance has plastic bars that protect the internal soft membrane inside the device.

Very thin waterproof membrane
So thin, that if it was picked up by a person, it would break. The benefit of this is that it will let sound through.

Below are the different shapes that the entry could be shaped.

Cone    Square-based pyramid    Tetrahedron (triangle-based pyramid)    Triangular prism

FIG. 3A

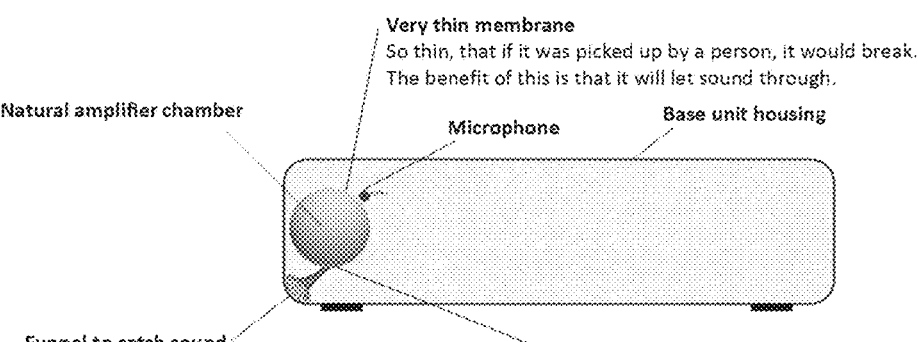

Very thin membrane
So thin, that if it was picked up by a person, it would break.
The benefit of this is that it will let sound through.

Natural amplifier chamber

Microphone

Base unit housing

Funnel to catch sound

Entry to the funnel is wide in order to catch the maximum
amount of sound. The funnel is also made of hard plastic
so it can't be broken if picked up.

Entry to the amplifier is at the bottom of the chamber.
The logic for this is that if water does get in, it automatically drains out.

NOTE:
The position of the opening does not have to be in this
location, this drawing is for concept demonstration only.

FIG. 3B

TECHNOLOGY CONFIGURED TO MONITOR CORRECT UTILIZATION OF A DISPENSED SUBSTANCE, INCLUDING DISPENSING UNITS HAVING ENVIRONMENTAL SENSORS

CROSS-REFERENCE TO RELATED APPLICATIONS

This application is a national phase entry under 35 U.S.C. § 371 of International Patent Application PCT/AU2021/050428, filed May 10, 2021, designating the United States of America and published as International Patent Publication WO 2021/226658 A1 on Nov. 18, 2021, which claims the benefit under Article 8 of the Patent Cooperation Treaty to Australian Patent Application Serial No. 2020901495, filed May 9, 2020, Australian Patent Application Serial No. 2020901712, filed May 27, 2020, Australian Patent Application Serial No. 2020904527, filed Dec. 7, 2020, and Australian Patent Application Serial No. 2021900361, filed Feb. 14, 2021.

TECHNICAL FIELD

The present disclosure relates, in various embodiments, to technology configured to monitor correct utilization of a dispensed substance, including dispensing units having environmental sensors. For example, this may include soap dispensers configured to monitor handwashing activity, and toothpaste dispensers configured to monitor brushing activity, and others. Embodiments include both base units, which are configured to operate with separate dispensing containers, and containers having electronic components built in. While some embodiments will be described herein with particular reference to those applications, it will be appreciated that the present disclosure is not limited to such a field of use, and is applicable in broader contexts.

BACKGROUND

Any discussion of the background art throughout the specification should in no way be considered as an admission that such art is widely known or forms part of common general knowledge in the field.

At present, the world is gripped by a COVID-19 pandemic. In this situation, there is a new heightened awareness and emphasis on personal hygiene, including handwashing. Whilst there are various known commercial systems that monitor handwashing activities, for example, in hospital and industrial settings, these are far too complex for basic household use.

It is an object of the present disclosure to overcome or ameliorate at least one of the disadvantages of the prior art, or to provide a useful alternative.

BRIEF SUMMARY

Example embodiments are described below in the section entitled "claims," and in the section entitled "detailed description."

One embodiment provides a device configured to monitor utilization of a dispensed substance, the device including: a unit configured to support or provide a container, the container being configured to contain a substance to be dispensed, wherein the substance is in use dispensed via a dispenser arrangement that is configured to transport the substance from the container to a location external of the container in response to interaction with the dispenser arrangement; electronic componentry mounted in the unit, the electronic componentry including: a dispensing monitoring sensor component configured to monitor dispensing of the substance; an environmental conditions sensor component configured to monitor environmental conditions; and a wireless communications module; an output module; wherein the output module is configured to cause the wireless communications module to transmit an output in response to: (i) identification by the dispensing monitoring sensor component dispensing of the substance; and/or (ii) identification by the environmental conditions sensor component of a prescribed set of environmental conditions being observed.

One embodiment provides a device wherein the output module is in communication with a computing device, and wherein the computing device is configured to identify correct utilization of the dispensed substance responsive to a predefined combination of (i) identification by the dispensing monitoring sensor component dispensing of the substance; and/or (ii) identification by the environmental conditions sensor component of a prescribed set of environmental conditions being observed.

One embodiment provides a device wherein the environmental conditions sensor component includes a microphone, and wherein identification by the environmental conditions sensor component of a prescribed set of environmental conditions includes identification of audible signals that are representative of correct utilization of the substance.

One embodiment provides a device wherein the audible signals that are representative of correct utilization of the substance include audible signals representative of hand washing.

One embodiment provides a device wherein the audible signals that are representative of correct utilization of the substance include audible signals representative of electric toothbrush operation One embodiment provides a device wherein the environmental conditions sensor component is configured to monitor for vibration, and wherein identification by the sensor component of a prescribed set of environmental conditions includes identification of vibration signals that are representative of correct utilization of the substance.

One embodiment provides a device wherein the dispensing monitoring sensor component includes a weight or pressure sensor.

One embodiment provides a device wherein the weight or pressure sensor is configured to detect a dispensing operation that includes downwards pressing on the dispensing arrangement.

One embodiment provides a device wherein the weight or pressure sensor is configured to detect a change in quantum of substance in the container.

One embodiment provides a device wherein the device includes the container and the dispensing arrangement.

One embodiment provides a device wherein the substance is a personal hygiene product.

One embodiment provides a device wherein the personal hygiene product is liquid soap.

One embodiment provides a device wherein the personal hygiene product is toothpaste.

One embodiment provides a device wherein the output module is in communication with a computing device, wherein the computing device executes a software application that is configured to identify: a dispensing event associated with environmental conditions representative of correct use of the dispensed substance.

One embodiment provides a device wherein the output module is in communication with a computing device, wherein the computing device executes a software application that is configured to identify: a dispensing event associated with environmental conditions representative of incorrect use of the dispensed substance.

One embodiment provides a device wherein the output module is in communication with a computing device, wherein the computing device executes a software application that is configured to identify: a dispensing event that is not associated with environmental conditions representative of incorrect use of the dispensed substance.

One embodiment provides a device wherein the output module is in communication with a computing device, wherein the computing device executes a software application that is configured to identify: environmental conditions that should be a precursor to a dispensing event, followed by a dispensing event.

One embodiment provides a device wherein the output module is in communication with a computing device, wherein the computing device executes a software application that is configured to identify: environmental conditions that should be a precursor to a dispensing event, followed by a threshold period without a dispensing event.

One embodiment provides a computer implemented method for monitor utilization of a dispensed substance, the method including receiving an output from a device as described herein, and processing that output thereby to predict whether correct utilization of a dispensed substance has occurred.

One embodiment provides a method wherein the correct utilization is determined based on environmental conditions monitored in a region surrounding the location of dispensing.

One embodiment provides a device configured to monitor utilization of a dispensed substance, the device including: a body configured to support or provide a container, the container being configured to contain a substance to be dispensed, wherein the substance is in use dispensed via a dispenser arrangement that is configured to transport the substance from the container to a location external of the container in response to manual interaction with the dispenser arrangement; electronic componentry mounted in the unit, the electronic componentry including: a sensor component configured to monitor dispensing of the substance; a sensor component configured to monitor environmental conditions; and a wireless communications module; an output module; wherein the output module is configured to cause the wireless communications module to transmit a predefined output in response to identification by the sensor component of a prescribed set of environmental conditions.

One embodiment provides a soap dispensing unit including: a container configured to contain a liquid soap product; a dispenser arrangement configured to transport the liquid soap product from the container to a location external of the container in response to activation by manual interaction with the dispenser arrangement; electronic componentry mounted in the unit, the electronic componentry including: a microprocessor; a sensor component configured to monitor environmental conditions; and a wireless communications module; wherein the microprocessor is configured to cause the wireless communications module to transmit a predefined signal in response to identification by the sensor component of a prescribed set of environmental conditions; wherein the predefined signal causes presentation by a software user interface operating on a mobile device of data representative of either: (i) compliant handwashing activity; or (ii) non-compliant handwashing activity.

One embodiment provides a soap dispensing unit monitor for a soap dispenser including: a container configured to contain a liquid soap product; a dispenser arrangement configured to transport the liquid soap product from the container to a location external of the container in response to activation by manual interaction with the dispenser arrangement; the monitor including electronic componentry mounted in the unit, the electronic componentry including: a microprocessor; a sensor component configured to monitor environmental conditions; and a wireless communications module; wherein the microprocessor is configured to cause the wireless communications module to transmit a predefined signal in response to identification by the sensor component of a prescribed set of environmental conditions; wherein the predefined signal causes presentation by a software user interface operating on a mobile device of data representative of either: (i) compliant handwashing activity; or (ii) non-compliant handwashing activity.

One embodiment provides a soap dispensing unit monitor for a soap dispenser including: a container configured to contain a liquid soap product; a dispenser arrangement configured to transport the liquid soap product from the container to a location external of the container in response to activation by manual interaction with the dispenser arrangement; the monitor including electronic componentry mounted in the unit, the electronic componentry including: a microprocessor; a sensor component configured to monitor environmental conditions; and an output module; wherein the output module is configured to cause the wireless communications module to transmit a predefined output in response to identification by the sensor component of a prescribed set of environmental conditions;

One embodiment provides a substance dispensing unit including: a body configured to support or provide a container, the container being configured to contain a substance to be dispensed; a dispenser arrangement configured to transport the substance product from the container to a location external of the container in response to activation by manual interaction with the dispenser arrangement; electronic componentry mounted in the unit, the electronic componentry including: a microprocessor; a sensor component configured to monitor environmental conditions; and an output module; wherein the output module is configured to cause the wireless communications module to transmit a predefined output in response to identification by the sensor component of a prescribed set of environmental conditions.

Reference throughout this specification to "one embodiment," "some embodiments" or "an embodiment" means that a particular feature, structure or characteristic described in connection with the embodiment is included in at least one embodiment of the present disclosure. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms "comprising," "comprised of" or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including" or "which includes" or "that includes" as used herein is also an open term that also means including at least the elements/features that follow the term, but not excluding others. Thus, "including" is synonymous with, and means, "comprising."

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the present disclosure will now be described, by way of example only, with reference to the accompanying drawings in which:

FIGS. 3A and 3B illustrate example microphone configuration arrangements.

DETAILED DESCRIPTION

Figure 1:
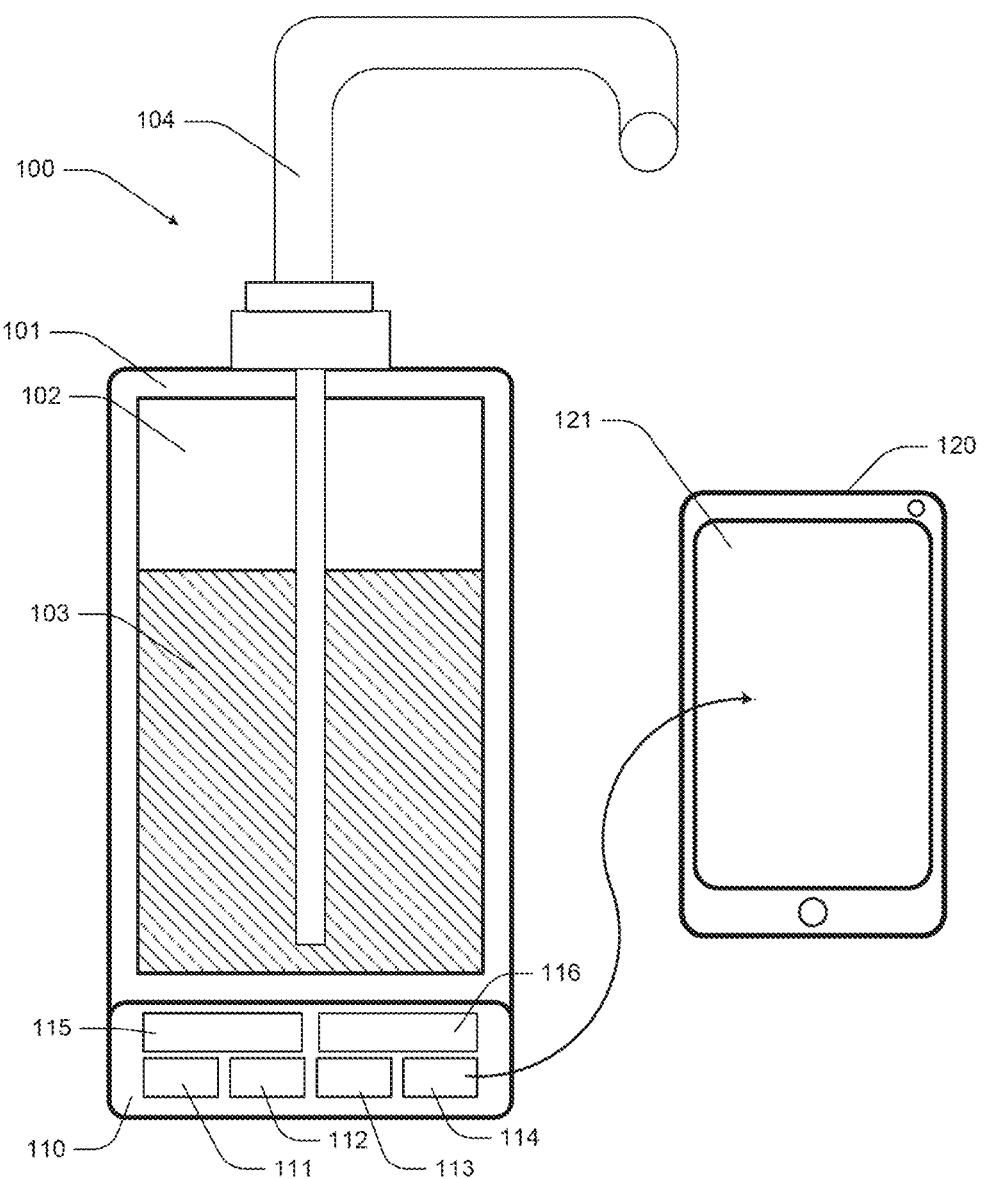
FIG. 1 illustrates a soap dispensing unit according to one embodiment.

The present disclosure relates, in various embodiments, to technology configured to monitor correct utilization of a dispensed substance, including dispensing units having environmental sensors. For example, this may include soap dispensers configured to monitor handwashing activity, and toothpaste dispensers configured to monitor brushing activity. Embodiments include both base units, which are configured to operate with separate dispensing containers, and containers having electronic components built in. While some embodiments will be described herein with particular reference to those applications, it will be appreciated that the present disclosure is not limited to such a field of use, and is applicable in broader contexts. For example, further embodiments relate to dispensing of toothpaste, and monitoring/reporting on tooth brushing activities.

Various embodiments relate to devices configured to monitor utilization of a dispensed substance. The substance may be a liquid, gel, paste, floss, or other substance. Examples considered herein are primarily described in relation to personal hygiene substances.

The devices each include a unit configured to support or provide a container. For instance, in some embodiments the devices are a base unit or the like into which a container is mounted, whereas in other embodiments the devices are integrated into a container. In each case, the container is configured to contain a substance to be dispensed. In use, for some embodiments, the substance is dispensed via a dispenser arrangement that is configured to transport the substance from the container to a location external of the container (in response to interaction with the dispenser arrangement). This may include a push-down dispenser, or another form of dispenser. In other embodiments the dispensing is via a manual withdrawal (for example, lifting soap from a soap holder).

The device includes electronic componentry mounted in the unit, the electronic componentry including:

A dispensing monitoring sensor component configured to monitor dispensing of the substance. In some embodiments, this is a pressure/weight sensor, which is configured to identify when a push-down dispenser is actuated. A wide range of other sensors may alternately be used.

An environmental conditions sensor component configured to monitor environmental conditions. In some embodiments, this includes a microphone, which is configured to identify particular sounds/audible signals in the area around the device. These are preferably representative of substance utilization (e.g., sounds representative of hand washing, sounds representative of tooth brushing, etc.).

A wireless communications module, for example, a WiFi module.

An output module, which is configured to provide signals over the wireless communication module in response to input from the sensors.

Preferably, the output module is configured to cause the wireless communications module to transmit an output in response to:

(i) identification by the dispensing monitoring sensor component dispensing of the substance; and/or (ii) identification by the environmental conditions sensor component of a prescribed set of environmental conditions being observed.

In preferred embodiments, the output module is in communication with a computing device, for example, a smartphone. This computing device is configured to, via a software application, identify correct utilization of the dispensed substance based on a combination of the dispensing and the environmental conditions around the time of dispensing. That is, the identification is made responsive to a predefined combination of (i) identification by the dispensing monitoring sensor component dispensing of the substance; and/or (ii) identification by the environmental conditions sensor component of a prescribed set of environmental conditions being observed. Specific use case examples include:

Identifying correct handwashing, based on dispensing of liquid soap followed by a threshold time period of audible signals representative of running water (or interrupted running water).

Identifying incorrect handwashing, based on dispensing of liquid soap, which is not followed by a threshold time period of audible signals representative of running water (or interrupted running water).

Identifying correct toilet hygiene, based on a toilet flush sound, followed by dispensing of liquid soap, followed by a threshold time period of audible signals representative of running water (or interrupted running water).

Identifying incorrect toilet hygiene, based on a toilet flush sound, which is not followed by dispensing of liquid soap and a threshold time period of audible signals representative of running water (or interrupted running water).

Identifying correct dental hygiene, based on dispensing of toothpaste, followed by a threshold time period of audible signals representative of tooth brushing (which may be a brushing sound, electric tooth brush sound, and/or running water sound).

Identifying incorrect dental hygiene, based on dispensing of toothpaste, which is not followed by a threshold time period of audible signals representative of tooth brushing (which may be a brushing sound, electric tooth brush sound, and/or running water sound).

A wide range of other use cases may be used, for example, in conjunction with other personal hygiene products such as mouthwash or dental floss. The above selection is representative only.

In practice, the device may be used by parents for the purposes of monitoring their children's hygiene habits. However, the technology may be employed for various other purposes.

Examples are described below, in particular, by reference to a soap dispensing and monitoring of handwashing. However, it will be appreciated that any examples provided in the context of soap/handwashing are able to be adapted to other purposes, for example, including toothpaste/brushing. Furthermore, whilst some embodiments are described by reference to units that include both container/dispenser hardware and electronic components, other embodiments provide base units or the like that provide electronic components, and are used in combination with traditional (non-instrumented) container/dispenser hardware FIG. 1 illustrates a soap dispensing unit 100 according to one embodiment. It should be appreciated that the shape and design of unit 100 is relatively generic, and that functional aspects of the technology described herein can be incorporated into a wide range of soap dispensing units having respective design and configuration elements. Furthermore, whilst unit 100 is illustrated as a battery powered unit, in another embodiment a soap dispensing unit is coupled to a wall power supply.

Unit 100 includes a body 101 that defines a container 102 configured to contain a liquid soap product 103. A dispenser arrangement 104 is configured to transport liquid soap product 103 from the container to a location external of the container in response to activation by manual interaction with the dispenser arrangement. For example, as illustrated in FIG. 1 the dispenser arrangement may be a push down suction arrangement. Alternate embodiments make use of other dispenser arrangements, including electronically actuated dispensers.

Electronic componentry is mounted in unit 100, for example, in a compartment 110. The manner by which the electronic components are mounted varies between embodiments. In some embodiments, compartment 110 is removable from body 101 (for example, via a snap-lock arrangement, screw arrangement, platform arrangement, or the like), thereby allowing for replacement of body 101 without replacing the electronic componentry.

The electronic componentry includes a microprocessor 111, which is configured to execute a stored set of software instructions thereby to enable the electronic componentry to perform various functionalities described herein. The electronic componentry further includes at least one sensor component configured to monitor environmental conditions. Examples of this sensor component are described in more detail further below. In the example of FIG. 1, a dispenser sensor 113 is provided, this being configured to identify activation of the dispenser arrangement (preferably including distinguishing full and partial activation, which may be used for improved accuracy in monitoring an amount of soap (or other substance) dispensed). A wireless communications module 114 is also provided, for example, a WiFi or Bluetooth module. In the illustrated example, compartment 110 contains a power supply 115, for example, a battery.

The dispenser sensor 113 may include a weight/pressure sensor in a base region of the device, which is configured to identify downward pressure on the device, which is representative of a "push down" to activate a dispenser. In some embodiments, the pressure sensor is configured to determine whether the pressure is representative of a "full press" or "half press," allowing for more accurate monitoring of an amount of soap dispensed. A weight/pressure sensor may also be used to monitor dispensing based on changes in weight that are influenced by a reduction in contained substance following each dispensing event.

One of the core functionalities of unit 100 is that the microprocessor is configured to cause the wireless communications module to transmit a predefined signal in response to identification by the sensor component of a prescribed set of environmental conditions. This predefined signal causes presentation by a software user interface 121 operating on a mobile device 120 of data representative of either: (i) compliant handwashing activity; or (ii) non-compliant handwashing activity. In practice, a user downloads an app, and couples that app with one or more instances of unit 100 (for example, via a coupling process that uses Bluetooth, NFC, WiFi, unique identifier input, or any other technique used in the context of home automation and IoT devices), and is provided information such as via notifications in relation to hand washing activity. This may be used for a range of purposes, including monitoring children, the elderly, people with disabilities, front line workers, and so on.

In a preferred embodiment, sensor component 112 includes a sensor component configured to monitor environmental conditions including ambient noises. This enables the unit, via operation of the microprocessor, to identify physical events according in the facility of the unit based on categorization of sounds. Detection of events based on audio analysis will be understood by those skilled in the art, with a range of technologies available. These include: (i) AI-trained systems that are able to perform classification of sounds; (ii) software that defines a waveform and/or waveform characteristics based on audio input and compares those to predefined samples; and (iii) other audio analysis technologies (including white noise detection).

In some embodiments, sensor component 112 is configured thereby to enable unit 100 to identify events including any one or more of the following:

A toilet flush.

Interrupted tap water flow (i.e., water from a tap being interrupted by the presence of hands being washed).

Uninterrupted tap water flow (i.e., water from a tap that is not interrupted by the presence of hands being washed).

Example use cases are described below.

In one embodiment, the electronic componentry is configured to identify ambient noise predicted to represent a toilet flush event. Based on that functionality, in combination with sensor 112, the electronic componentry is configured to associate to a common event data set: (i) an identified toilet flush event; and (ii) presence/absence of activation of the dispenser arrangement within a predefined time period from the identified toilet flush event. This allows for the mobile app to provide a notification that the toilet was flushed, and that that soap was used (or not used) afterwards.

In another embodiment, the sensor component configured to monitor environmental conditions including ambient noises is additionally configured to identify ambient noise predicted to represent interrupted tap water flow. In this example, the electronic componentry is configured to associate to a common event data set: (i) an identified toilet flush event; and (ii) presence/absence of activation of the dispenser arrangement within a predefined time period from the identified toilet flush event; and (iii) presence/absence of a threshold time period of interrupted tap water flow within a predefined time period (for example, 30 seconds) of the identified toilet flush event or the activation of the dispenser arrangement within a predefined time period from the identified toilet flush event. This allows for the mobile app to provide a notification that the toilet was flushed, that that soap was used (or not used) afterwards, and that there was a threshold period of handwashing (or not).

Figure 2A:
FIG. 2A illustrates an example screenshot for a mobile app according to one embodiment.
Figure 2B:
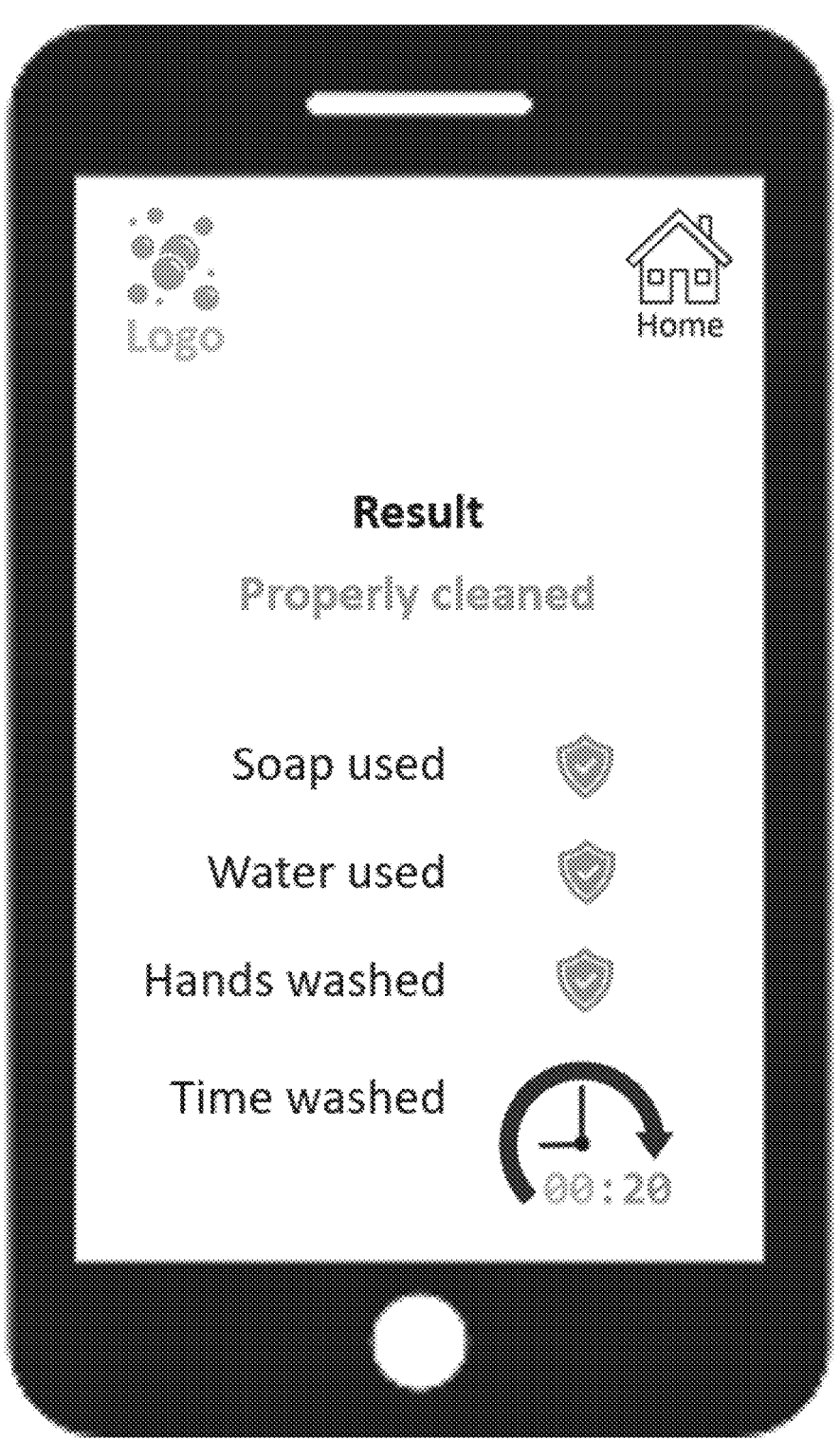
FIG. 2B illustrates an example screenshot for a mobile app according to one embodiment.

The above use case is extended, in some embodiments, such that the sensor component configured to monitor environmental conditions including ambient noises is additionally configured to identify ambient noise predicted to represent uninterrupted tap water flow. In this example, the electronic componentry is configured to associate to a common event data set: (i) an identified toilet flush event; and (ii) presence/absence of activation of the dispenser arrangement within a predefined time period from the identified toilet flush event; (iii) presence/absence of a threshold time period of interrupted tap water flow within a predefined time period of the identified toilet flush event or the activation of the dispenser arrangement within a predefined time period from the identified toilet flush event; and (iv) presence/absence of a threshold time period of uninterrupted tap water flow within a predefined time period of the identified toilet flush event or the activation of the dispenser arrangement within a predefined time period from the identified toilet flush event. This may result in a notification screen such as that on FIG. 2A, which provides data representative of a common event, with confirmation of presence/absence of: toilet flush; soap use; water use; and hand washing (via water interrupt sound). An alternate embodiment screenshot is shown in FIG. 2B, this excluding the flush monitoring functionality.

In some embodiments, the device includes a signaling system, for example, one of more LEDs, thereby to provide a visual indicator of operation. In one example, this includes the following:

Push dispenser (red light, no countdown).
Observe flowing water sound (red light, no countdown).
Observe hand washing sound, such as interrupted water flow (Red light, with countdown started).
Light and/or sound when hand washing sound observed for a set amount of time (green light).

In a further embodiment, the electronic componentry is configured to identify ambient noise predicted to represent interrupted tap water flow, and associate to a common event data set: (i) activation of the dispenser arrangement; and (ii) presence/absence of a threshold time period of interrupted tap water flow within a predefined time period of the activation of the dispenser arrangement. This allows for handwashing compliance monitoring independent of a toilet flush event. Optionally, sensor 112 is activated only following triggering of sensor 113, thereby allowing for improved conservation of power.

In an alternate embodiment, the device dispenses toothpaste, and the electronic componentry is configured to identify ambient noise predicted to represent tap water flow and/or interrupted tap water flow for a threshold time following dispensing (the sound may commence prior to dispensing).

In some embodiments, a vibration sensor is used as an alternate to a microphone (or in combination with a microphone), thereby to monitor for compliance activity. It will be appreciated that, assuming the device is positioned adjacent a basin, water flow can be detected through vibrations.

It will be appreciated that in each of the examples above, the wireless communications module 114 transmits a predefined signal in response to identification by the sensor component of a prescribed set of environmental conditions such that the predefined signal causes presentation by software user interface 121 operating on mobile device 120 of data representative of the common event data set, thereby to provide an indication of: (i) compliant handwashing activity; or (ii) non-compliant handwashing activity. Preferably, module 114 is actuated only periodically to enable to transmission of signals when required, and otherwise is deactivated or placed in a low-power sleep mode (or optionally in a mode that continues to observe for defined environmental conditions, such as sounds that trigger activation from the sleep mode).

It will further be appreciated that various app functionalities are a matter of design choice, for example, events that give rise to notifications (for example, a toilet flush with non-compliant handwashing).

Software user interface 121 is preferably operable to enable coupling with the unit, and user designation of an identifier for the unit. For example, a user performs a coupling process (for example, a standard Bluetooth coupling, input of a unique ID, or the like) and assigns the unit a designation (for example, "downstairs bathroom" or the like). This allows for a user to configure their app to monitor soap dispensers at multiple locations in a house.

In some embodiments, the electronic circuitry is configured to monitor a capacity status for the container, and provide a signal in response to the capacity status passing a threshold. The capacity status passing a threshold is in some cases determined based on a counter that is incremented in response to input from a sensor that is triggered by activation of the dispenser arrangement, or by a further sensor placed inside (or otherwise on) the container that is configured to identify soap levels below a prescribed level. This capacity signal may be provided to the mobile device, for example, to inform a user that it is time to procure more soap. This signal may trigger an ordering process, which streamlines (or in some cases automated) ordering of additional soap upon the threshold being reached. This may include a container configured to allow refilling of unit 100.

FIGS. 3A and 3B illustrate example microphone configuration arrangements for use with a dispenser such as unit 100 of FIG. 1 (or a standalone compartment 110 that serves as a base unit into which a container is placed thereby to function as a unit 100).

As noted above, embodiments considered herein make use of a sound sensor to monitor activities associated with the dispensing of soap or another material. Configuration of a microphone to distinguish sounds without being especially susceptible to water ingress is a useful feature. This design allows the user to wash the device and have the water automatically drain away clearing the water away from the microphone. FIGS. 3A and 3B provide examples.

In the example of FIG. 3A, an aperture is formed in the sidewall of a base unit (for example, compartment 110 of FIG. 1) that houses electronic components, including a microphone. The aperture is tapered to serve as an amplifier, in order to capture a maximum amount of sound at the external surface, yet minimize aperture size at the internal surface. A membrane plug formed of a very thing waterproof membrane is inserted into the aperture/entrance, and FIG. 3A shows various shapes. Protective bars (for example, plastic) are provided to protect the membrane.

In the example of FIG. 3B, a funnel upwardly extended from the sidewall of the base unit, preferably from adjacent the base of the base unit. An amplifier chamber is provided internally of the base unit, this having a thin waterproof membrane adjacent the microphone. The amplifier chamber connects to the funnel at its lower extremity, such that any water that entered the chamber drains out naturally when the base unit is standing as intended.

As noted, in some embodiments, the dispenser is configured to dispense toothpaste, and the electronic componentry configured to monitor for predicted tooth brushing activity (for example, based on audible signals, which may include water flow and/or the sound of an operating electric or non-electric toothbrush). In some such embodiments, an additional sensor is provided thereby to identify a unique tooth brushing device that is used in connection with the dispenser, for example, to allow monitoring the tooth brushing activities of two distinct people having their own tooth brush devices. This may be achieved via a range of sensor arrangements, including:

> A toothbrush docking station, with multiple docking locations configured to store respective toothbrush devices, and a sensor configured to identify which of the toothbrush devices is removed and/or replaced from the docking locations. Each toothbrush device (and/or docking location) is associated with a unique user, for example, by way of a configuration process performed via a user interface delivered through the smartphone application described above. Logic in computer programming is configured such that a given toothpaste dispensing event is associated with a user for whom the associated toothbrush device/docking location was most recently accessed. The programming logic may also be configured to identify where there are multiple tooth brush devices accessed followed by multiple dispensing events, thereby to track brushing activity of multiple users concurrently.

> Unique proximity tags, for example, RFID tags, in each tooth brushing device (for example, in a disposable brush head of an electric toothbrush). When toothpaste is dispensed onto a tooth brushing device having one of those tags, the dispensing device reads the tag and is able to uniquely associate observed brushing activity to a unique user. A configuration process is performed via the smartphone app thereby to register a newly presented tag to a unique user (for example, when a new tag is presented, the dispensing device is configured to cause the smartphone app to deliver a notification prompting a user to associate that tag/device to a user, which may be a new user or a previously defined user).

In a further embodiment, the technology described above is adapted to operate additionally/alternately with dispensing of dental floss and/or mouthwash. This may include a sensor that is configured to monitor for extraction of a length of floss (for example, a contact sensor), and/or a sensor that is configured to monitor for dispensing of mouthwash (for example, an accelerometer that observes tipping of the device). The programming logic may be configured to track and report on dispensing of floss and/or mouthwash relative to observed tooth brushing activities. For example, the software application may provide a report showing: "USER; BRUSHING SUCCESSFUL; MOUTHWASH USED; FLOSS USED."

In a further embodiment, observation of brushing activity is omitted, with the device instead focused on observing and reporting on a user accessing all three of floss, toothpaste and mouthwash within a predefined window of time (and optionally in a defined sequence).

In some embodiments, brushing operation, and/or operation of other equipment (for example, a flossing device) is monitored by way of an accelerometer/IMU/other sensor attached to the equipment.

It should be appreciated that in the above description of exemplary embodiments of the present disclosure, various features of the present disclosure are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the present disclosure, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out embodiments of the present disclosure.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the present disclosure, those skilled in the art will recognize that other and further modifications may be made thereto without departing from the spirit of the present disclosure, and it is intended to claim all such changes and modifications as falling within the scope of the present disclosure. For example, any formulas given above are merely representative of procedures that may be used. Functionality may be added or deleted from the block diagrams and operations may be interchanged among functional blocks. Steps may be added or deleted to methods described within the scope of the present disclosure.

The invention claimed is:

1. A device configured to monitor utilization of a dispensed substance, the device including:

a unit configured to support or provide a container, the container being configured to contain a substance to be dispensed, wherein the substance to be dispensed is hand soap;

electronic componentry mounted in the unit, the electronic componentry including:

a dispensing monitoring sensor component configured to monitor for primary events representative of dispensing of the hand soap;

an environmental conditions sensor component configured to monitor environmental conditions, wherein the environmental conditions sensor component is configured to collect audio data, and wherein the audio data is processed to identify secondary events representative of each of the following secondary event categories:

i. the secondary event category representative of identification of flushing of a toilet based on processing of audio data; and ii. the secondary event category representative of identification of hands being washed under running water for a threshold period of time based on processing of audio data;

a wireless communications module; and an output module;

wherein the device is configured to cause presentation on an external device of data that is generated based upon the identification of primary events and secondary events and determination of temporal association between the primary events and the secondary events, including secondary events representative of the following secondary event categories:

i. the secondary event category representative of identification of flushing of a toilet based on processing of audio data; and ii. the secondary event category representative of identification of hands being washed under running water for the threshold period of time based on processing of audio data;

wherein the presentation on the external device of data that is generated based upon the identification of primary events and secondary events includes presentation of data based on relationships between temporally associated primary and secondary events, thereby presenting via a user interface compliance or non-compliance with a predefined event flow;

wherein compliance with the predefined event flow comprises all of the following:

i. a first event belonging to the secondary event category representative of identification of the flushing of a toilet based on processing of audio data;

ii. within a first predefined time period following the first event, a second event being a primary event representative of dispensing of the hand soap; and iii. within a second predefined time period following the second event, a third event belonging to the secondary event category representative of identification of hands being washed under running water for the threshold period of time based on processing of audio data; and wherein non-compliance with the predefined event flow comprises any one or more of the following:

i. the first event belonging to the secondary event category representative of identification of flushing of a toilet based on processing of audio data, but without, within the first predefined time period following the first event, the second event being the primary event representative of dispensing of the hand soap; and ii. the first event belonging to the secondary event category representative of identification of flushing of a toilet based on processing of audio data and, within the first predefined time period following the first event, the second event being the primary event representative of dispensing of the hand soap, but without, within the second predefined time period following the second event, the third event belonging to the secondary event category representative of identification of hands being washed under running water for the threshold period of time based on processing of audio data.

2. The device of claim 1, wherein the substance is in use dispensed via a dispenser arrangement that is configured to transport the substance from the container to a location external of the container in response to interaction with the dispenser arrangement.

3. The device of claim 1, wherein the environmental conditions sensor component is configured to monitor for vibration, and wherein identification by the sensor component of a prescribed set of environmental conditions includes identification of vibration signals that are representative of correct utilization of the substance.

4. The device of claim 1, wherein the dispensing monitoring sensor component includes a weight or pressure sensor.

5. The device of claim 4, wherein the weight or pressure sensor is configured to detect a dispensing operation that includes downwards pressing on a dispensing component.

6. The device of claim 4, wherein the weight or pressure sensor is configured to detect a change in quantum of substance in the container.

7. The device of claim 1, wherein the device includes the container and a dispensing member.

8. The device of claim 1, wherein the output module is in communication with a computing device, wherein the computing device executes a software application that is configured to identify: a dispensing event associated with environmental conditions representative of correct use of the dispensed substance.

9. The device of claim 1, wherein the output module is in communication with a computing device, wherein the computing device executes a software application that is configured to identify: a dispensing event associated with environmental conditions representative of incorrect use of the dispensed substance.

10. The device of claim 1, wherein the output module is in communication with a computing device, wherein the computing device executes a software application that is configured to identify: a dispensing event that is not associated with environmental conditions representative of incorrect use of the dispensed substance.

11. The device of claim 1, wherein the output module is in communication with a computing device, wherein the computing device executes a software application that is configured to identify: environmental conditions that should be a precursor to a dispensing event, followed by a dispensing event.

12. The device of claim 1, wherein the output module is in communication with a computing device, wherein the computing device executes a software application that is configured to identify: environmental conditions that should be a precursor to a dispensing event, followed by a threshold period without a dispensing event.

13. A computer implemented method for monitoring utilization of a dispensed substance, the method including receiving an output from a device according to claim 1, and processing that output thereby to predict whether correct utilization of a dispensed substance has occurred.

14. The method of claim 13, wherein the correct utilization is determined based on environmental conditions monitored in a region surrounding the location of dispensing.

\* \* \* \* \*